United States Patent [19]

Carrier et al.

[11] Patent Number: Plant 7,645

[45] Date of Patent: Sep. 10, 1991

[54] ALSTROEMERIA NAMED CYNTHIA

[75] Inventors: Leonard E. Carrier, Encinitas, Calif.; Stephen Garton, West Jordan, Utah

[73] Assignee: Native Plants, Inc., Salt Lake City, Utah

[21] Appl. No.: 511,789

[22] Filed: Apr. 20, 1990

[51] Int. Cl.[5] ..... A01H 5/00
[52] U.S. Cl. ..... Plt./68
[58] Field of Search ..... Plt./68

*Primary Examiner*—Howard J. Locker

*Attorney, Agent, or Firm*—Venable, Baetjer, Howard & Civiletti

[57] ABSTRACT

This plant is particularly characterized by its dwarf habit which makes the plant eminently suitable for cultivation as a potted plant. In addition, the plant bears several flowering stalks which carry large attractive flowers which are predominantly of a rich purple-pink coloration. The attractive flowers and desirable growth habit of this plant provide a novel addition to the range of Alstroemerias.

1 Drawing Sheet

BACKGROUND OF THE NEW PLANT

This new variety of Alstroemeria originated as a seedling resulting from crossing two plants growing among a collection of breeding stock maintained in a greenhouse in Encinitas, Calif. The seedling was selected for further propagation and testing because of the dwarf characteristic of the whole plant, and the attractive color of the many large flowers contained in several inflorescences as the plant bloomed in a pot. The select plant was propagated in Salt Lake City, Utah, by division of the rhizomatous rootstock and through tissue culture. The distinguishing characteristics of the new plant hold true in successive vegetative generations and appear to be firmly fixed. Propagation work is currently being carried out in Salt Lake City using tissue culture methods.

DESCRIPTION OF THE DRAWING

This new variety of Alstroemeria plant is illustrated by the accompanying photographic drawing in full color showing a blooming umbel of the plant with buds and flowers in different stages of flower development. The color renditions are believed to be as close to the specified color as is possible to obtain by conventional photographic procedures.

DESCRIPTION OF THE NEW PLANT

The following is a detailed description of the new Alstroemeria variety with color designations according to the The R.H.S. Colour Chart of The Royal Horticultural Society of London, England. The observations were made on plants grown in a greenhouse in Utah county, Utah, during the summer.

THE PLANT

Origin: Seedling (73-RP-70A).
Parentage:
*Seed parent.*—Breeding stock plant No. RP.
*Pollen parent.*—Breeding stock plant No. 70A.
Classification: Alstroemeria hybrid.
Form: Compact, erect bush with a slightly spreading habit having several flower stalks bearing branches with simple umbel arrangement at the tops.
Height: About 35 to 50 cm.

Growth: Erect, vigorous and strong.
Rootstock: Rhizomatous, the rhizomes bear numerous buds which give rise to vegetative and reproductive shoots throughout the growth period. Rhizomes also produce roots, some of which become tuberous.
Foliage:
*Quantity.*—Medium, 20 to 40 leaves per stem.
*Leaf size.*—About 10 cm.
*Leaf shape.*—Elliptical.
*Texture.*—Waxy.
*Color.*—Upper surface — Dark green. Lower surface — Grey green.

THE BUD

Form: Pear-shaped. The six petals are perianth and there is no calyx.
Size: Medium.
*Diameter.*—1.0 cm.
*Length.*—1.7 cm.
Length of peduncle: 2.0 cm.

THE FLOWER

Blooming habit: Continuous and freely flowering throughout the season.
Flower size: Medium.
*Diameter.*—About 5.5 cm.
*Length.*—About 6.0 cm.
Shape: Generally funnel-like.
Borne: Singly.
Petalage:
*Number.*—Six.
*Arrangement.*—Two concentric circles of three.
*Form.*—Outer petals — Obcordate. Inner petals — Elliptical.
*Texture.*—Smooth.
*Appearance.*—Satiny.
*Color.*—Outer Petals: The distal portion is red-purple, 64B, the mid portion is darker, 64A, and the base is lighter, 64C. Centrally, on the distal margin is a small green protruberance. The reverse surface is red-purple, 71C, with at least 3 green veins prominent in the distal part. Inner petals: Upper; The general color is red-purple; the distal portion is 64B, and the base is 64C. There is a small area of yellow, 3B, in the middle with a moderate number of greyed-purple streaks, 187A. The reverse surface is 63B, at the distal end and 63C, at the base, with a small area of pale green visible in the center. Lower; The general color is red-purple, 64B, with a very pale green area toward the base. There are some small greyed-purple streaks, 187A, in the center of the petal.

Persistence: The flowers hang and dry.

Lasting quality: On the plant, 14–18 days.

Main stem or stalk:

*Length.*—35 to 40 cm.

*Color.*—Dark green.

*Character.*—Upright, strong and thick.

REPRODUCTIVE ORGANS

Stamens:

*Number.*—Six.

*Arrangement.*—One opposite each petal.

*Anthers.*—Size: 5.0 mm. Color: Beige.

*Filaments.*—Length: About 4.0 cm. Color: Pink.

*Pollen.*—Color: Grey.

Pistils:

*Number.*—One.

*Style.*—Length: About 4.0 cm. Color: Pink.

*Stigma.*—Color: Pink.

Fruit:

*Shape.*—Capsular.

*Color.*—Light brown at maturity.

What is claimed:

1. A new and distinctive Alstroemeria hybrid, substantially as shown and described herein, characterized by a dwarf habit and large purple-pink colored flowers which are borne in attractive infloresences on relatively dwarf flower stalks.

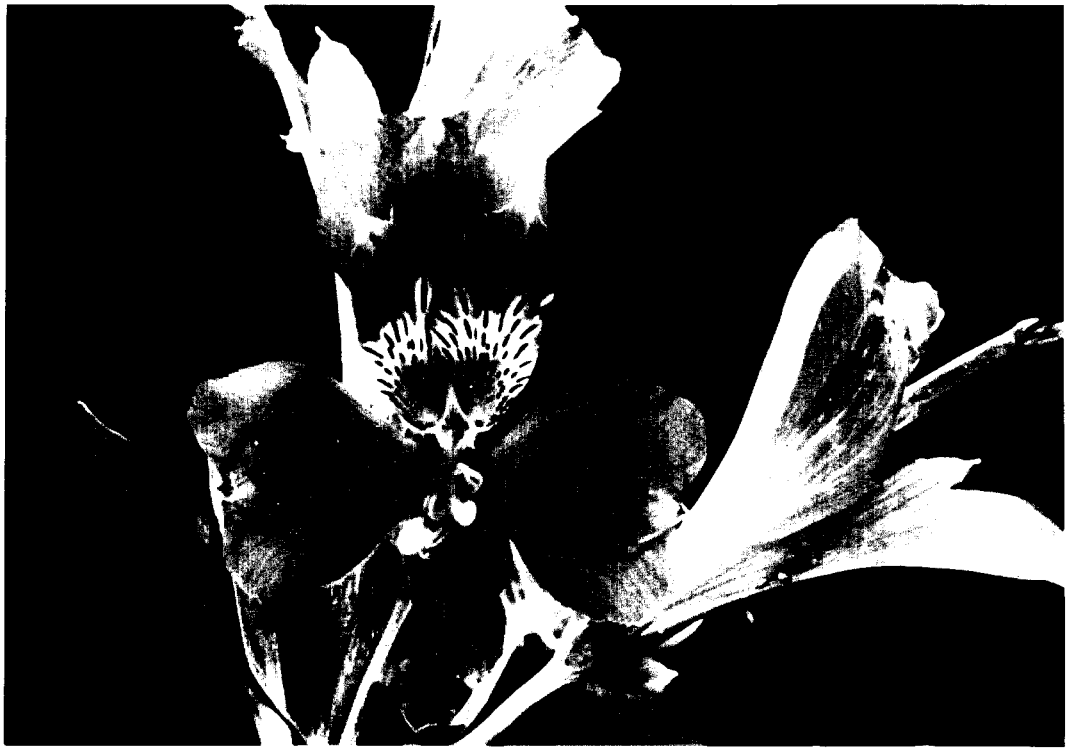

* * * * *